(12) United States Patent
Tono et al.

(10) Patent No.: US 7,269,308 B2
(45) Date of Patent: Sep. 11, 2007

(54) OPTICAL WAVEGUIDE TYPE BIOCHEMICAL SENSOR CHIP AND METHOD OF MANUFACTURING THE SAME

(75) Inventors: Ichiro Tono, Yokohama (JP); Kayoko Oomiya, Yokohama (JP); Tomohiro Takase, Sagamihara (JP); Ikuo Uematsu, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 5 days.

(21) Appl. No.: 11/393,771

(22) Filed: Mar. 31, 2006

(65) Prior Publication Data

US 2007/0081758 A1 Apr. 12, 2007

(30) Foreign Application Priority Data

Sep. 29, 2005 (JP) ............................. 2005-285586

(51) Int. Cl.
*G02B 6/00* (2006.01)
(52) U.S. Cl. .......................................... 385/12; 385/37
(58) Field of Classification Search ................. 385/12, 385/37
See application file for complete search history.

(56) References Cited

U.S. PATENT DOCUMENTS

| | | | |
|---|---|---|---|
| 5,082,629 A * | 1/1992 | Burgess et al. .......... 422/82.11 |
| 6,078,705 A * | 6/2000 | Neuschafer et al. .......... 385/12 |
| 6,395,558 B1 * | 5/2002 | Duveneck et al. .......... 436/172 |
| 6,429,022 B1 * | 8/2002 | Kunz et al. .................. 436/164 |
| 6,469,785 B1 * | 10/2002 | Duveneck et al. .......... 356/244 |
| 6,823,112 B2 * | 11/2004 | Deliwala ..................... 385/37 |
| 7,054,514 B2 * | 5/2006 | Uchiyama et al. ............ 385/12 |

FOREIGN PATENT DOCUMENTS

| | | |
|---|---|---|
| JP | 8-285851 | 11/1996 |
| JP | 9-61346 | 3/1997 |
| JP | 3236199 | 9/2001 |
| JP | 2004-333250 | 11/2004 |

* cited by examiner

*Primary Examiner*—Ellen E. Kim
(74) *Attorney, Agent, or Firm*—Oblon, Spivak, McClelland, Maier & Neustadt, P.C.

(57) ABSTRACT

An optical waveguide type biochemical sensor chip includes a light beam transmittable substrate having at least a first optical element that allows light beam to be impinged to the inside and a second optical element that emits light beam from the inside, an optical waveguide layer that is formed on a main surface of the substrate on which at least one of the first and second optical elements is formed, has a thickness of 3 to 300 µm and is made of a polymer resin material having a higher refractive index than that of the substrate material, and a sensing membrane that is formed on the optical waveguide layer and creates a reaction product having the ability of absorbing the light beam or an evanescent wave of the light beam in response to an introduced specimen.

17 Claims, 4 Drawing Sheets

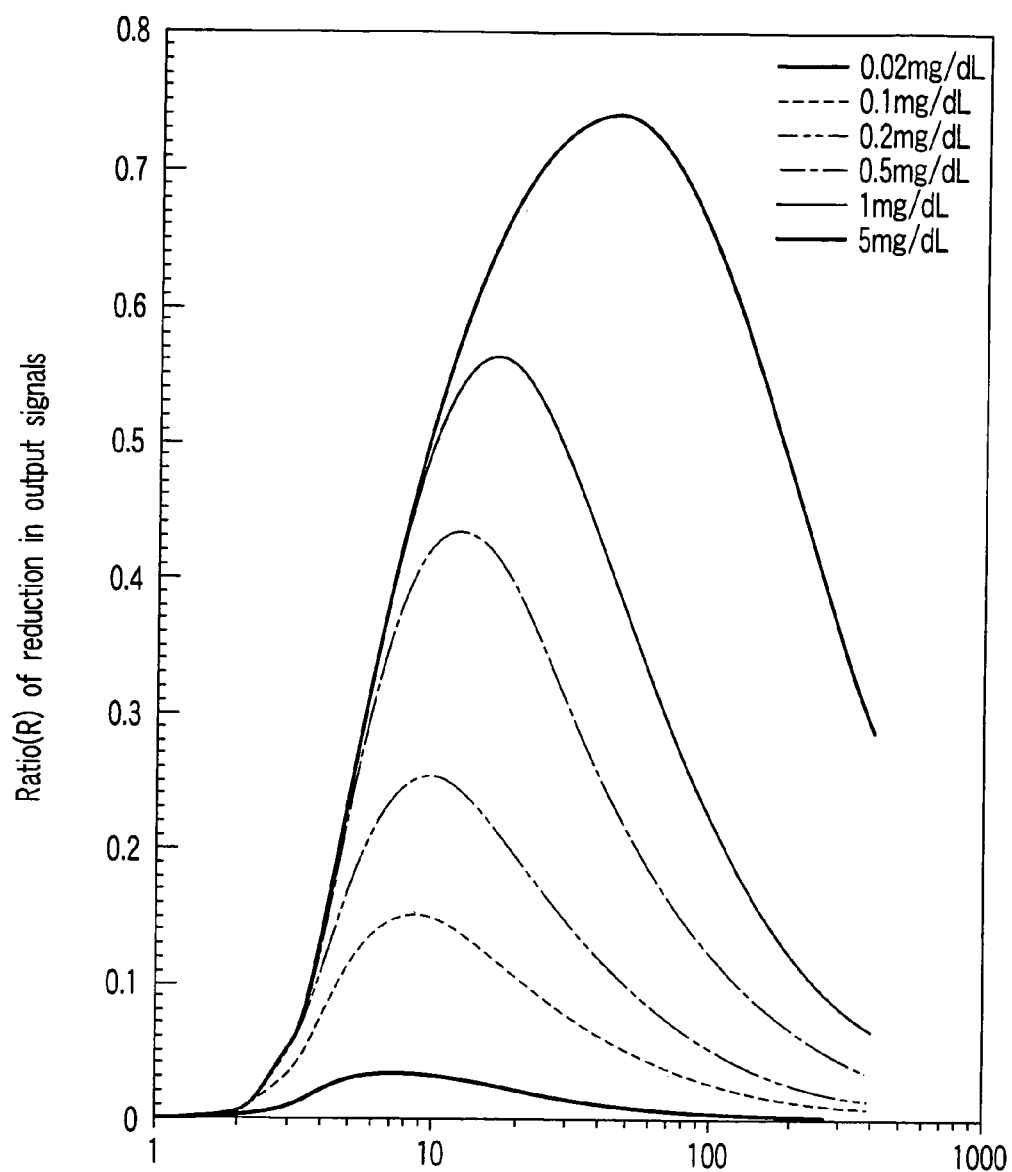
FIG. 4　Thickness of optical waveguide layer [μm]
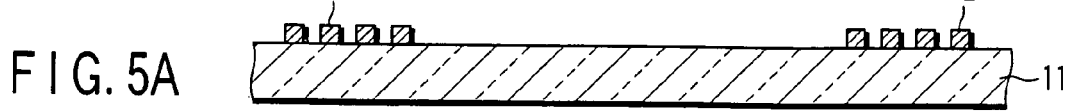
FIG. 5A
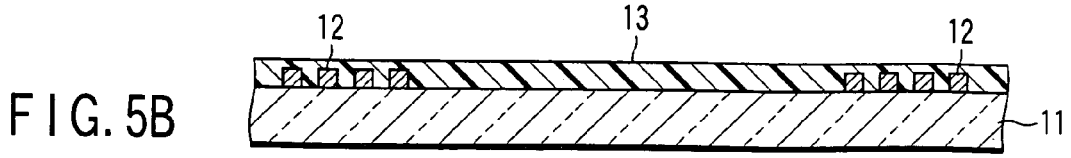
FIG. 5B

OPTICAL WAVEGUIDE TYPE BIOCHEMICAL SENSOR CHIP AND METHOD OF MANUFACTURING THE SAME

CROSS-REFERENCE TO RELATED APPLICATIONS

This application is based upon and claims the benefit of priority from prior Japanese Patent Application No. 2005-285586, filed Sep. 29, 2005, the entire contents of which are incorporated herein by reference.

BACKGROUND OF THE INVENTION

1. Field of the Invention

The present invention relates to an optical waveguide type biochemical sensor chip and a method of manufacturing the optical waveguide type biochemical sensor chip, and particularly to an optical waveguide type biochemical sensor chip for measuring the amount and properties of the biomolecule of organisms in an aqueous solution quantitatively and to a method of manufacturing the optical waveguide type biochemical sensor chip.

2. Description of the Related Art

Planar optical waveguide type biochemical sensor chips that are provided with a grating and a sensing membrane having a biomolecule recognition function and an information transformation function and utilize an evanescent wave arising on the surface of an optical waveguide layer have been proposed as small-sized and highly sensitive biochemical sensor chips.

In, for example, Jpn. Pat. Appln. KOKAI Publication No. 8-285851, a fluorescent immune sensor is disclosed which has a structure in which an optical waveguide layer made of a silicon oxide film having a film thickness of 620 nm is formed on a substrate by a sol-gel method and gratings are formed on both ends of the waveguide layer. There is a description in this publication that a polyimide film may be used as the optical waveguide layer. However, there is no disclosure of the details.

Also, in Jpn. Pat. Appln. KOKAI Publication No. 9-61346, a planar optical waveguide type biochemical sensor chip is disclosed which has a structure in which gratings are formed in the vicinities of both ends of a substrate and an optical waveguide layer is formed on the surface of the substrate including the gratings. In this publication, there is a description that this optical waveguide layer is preferably a film of silicon nitride, aluminum oxide, tantalum oxide manufactured by a sputtering method or a CVD method, or a glass film manufactured by an ion exchange method. An optical waveguide layer made of a similar material is disclosed in Jpn. Pat. No. 3236199.

Jpn. Pat. Appln. KOKAI Publication No. 2004-333250 discloses an optical waveguide sensor in which a sensing membrane having a biomolecule recognition function and an information transformation function is formed on a main surface of a glass substrate of 1 mm or less in thickness, wherein light beam is made to propagate within the substrate and to reflect on the substrate-sensing membrane interface.

Each of the optical waveguide layers described in the aforementioned three documents is formed in a thickness of about 1 μm depending on its material and forming method. On the other hand, as the wavelength of light beam from a light source, those ranging from the near ultraviolet region to the visible region are used in general. Therefore, the thickness of about 1 μm is a value once to four times the thickness of the wavelength of the propagated light beam.

In the optical waveguide layer having such a low thickness, the native mode number (eigenmode) determined by each refractive index of a core layer and a clad layer and by the wavelength of incident light beam, that is, the number of incident angles enabling the light beam to be impinged with optical elements for impinging light beam, for example, the grating, is a discontinuous value less than 10. It is therefore necessary to adjust the incident angle strictly corresponding to this discontinuous value.

Also, light beam propagated in a planar optical waveguide layer is generally attenuated, for example, by diffusion at the interface between the optical waveguide layer and the clad layer. Accordingly, the number of reflections is increased with a decrease in the film thickness of the optical waveguide layer, resulting in a decrease in the intensity of the light beam to be emitted. In a biochemical sensor with an optical waveguide layer having the above thickness, the number of reflections on the surface and interface (interface between the substrate and the sensing membrane) in the optical waveguide layer is increased. Therefore, the intensity of the emitting light beam attenuates and the emitting light beam tends to be affected by extraneous light beam and noise caused by, for example, the fluctuation of the system of measurement. As a result, the problem arises that a high power light source is required to obtain actual intensity of the emitted light beam, which renders it difficult to make the whole measuring system small-sized.

Also, in an optical waveguide in which light beam is propagated while totally reflecting within a glass substrate as described in the aforementioned Jpn. Pat. Appln. KOKAI Publication No. 2004-333250, the thickness of the glass substrate is set to about 0.7 mm to 1 mm in order to propagate light beam. The number of reflections on the interface between the glass substrate and the sensing membrane is decreased to a few, and detecting sensitivity is therefore lowered. If the thickness of the glass is decreased to raise the sensitivity, this reduces physical strength, bringing about handling difficulty.

In order to utilize such an optical waveguide type biosensor chip, it is desired to use a light source, such as a laser diode, that has a low power but is small and inexpensive as the light source of the light beam which is to be impinged to the chip. In order to make it possible to utilize this light source, it is necessary to make the optical waveguide layer have a proper thickness as mentioned above and also to raise the light beam impinging and emitting efficiency.

Moreover, light beam is diffused by, for example, scratches and contamination of optical elements such as a grating, leading to decreased coupling efficiency.

In the foregoing publication of Jpn. Pat. Appln. KOKAI Publication No. 8-285851, there is a description of examples in which a grating is formed by lithography on the surface of an optical waveguide layer formed of silicon oxide or polyimide by a sol gel method. However, the surface of the grating is brought into contact with the air and therefore, the efficiency is not always high, and also no device to prevent damage and contamination to the grating part is shown.

Also, in the case where the substrate is removed and processed to form a grating structure as described in the example of the aforementioned Pat. No. 3236199, a difference in refractive index between the substrate and the optical waveguide layer is decreased, resulting in reduced diffraction efficiency.

BRIEF SUMMARY OF THE INVENTION

According to a first aspect of the present invention, there is provided an optical waveguide type biochemical sensor chip, comprising:

a light beam transmittable substrate having at least one of a first optical element which allows light beam to be impinged to the inside and a second optical element which emits light beam from the inside;

an optical waveguide layer which is formed on a main surface of the substrate on which at least one of the first and second optical elements is formed, has a thickness of 3 to 300 µm and is made of a polymer resin material having a higher refractive index than that of the substrate material; and a sensing membrane which is formed on the optical waveguide layer and creates a reaction product having the ability of absorbing light beam or an evanescent wave of light beam in response to an introduced specimen.

According to a second aspect of the present invention, there is provided a method of manufacturing an optical waveguide type biochemical sensor chip, comprising:

forming at least one of a first optical element which allows light beam to be impinged to the inside and a second optical element which emits light beam from the inside on a light beam transmittable substrate;

forming an optical waveguide layer of 3 to 300 µm in thickness by applying a polymer resin material having a higher refractive index than that of the substrate on a main surface of the substrate on which at least one of the first and second optical elements is formed, and by drying; and forming a sensing membrane which creates a reaction product having the ability of absorbing light beam or an evanescent wave of light beam in response to a specimen introduced into the optical waveguide layer.

According to a third aspect of the present invention, there is provided a method of manufacturing an optical waveguide type biochemical sensor chip, comprising:

forming at least one of a first optical element which allows light beam to be impinged to the inside and a second optical element which emits light beam from the inside on a light beam transmittable substrate;

forming an optical waveguide layer of 3 to 300 µm in thickness by applying a polymer resin material having a higher refractive index than that of the substrate on a main surface of the substrate on which at least one of the first and second optical elements is formed, and drying;

forming a polymer resin layer having the same material and the same thickness as those of the optical waveguide layer on a surface opposite to the main surface of the substrate; and forming a sensing membrane which creates a reaction product having the ability of absorbing light beam or an evanescent wave of light beam in response to a specimen introduced into the optical waveguide layer.

BRIEF DESCRIPTION OF THE SEVERAL VIEWS OF THE DRAWINGS

FIG. 4 is a graph showing the dependency of the ratio of a reduction in output signals on the film thickness of an optical waveguide layer in the optical waveguide type biochemical sensor chip according to the first embodiment of the present invention;

FIGS. 5A, 5B, 5C and 5D are sectional views showing steps of producing the optical waveguide type biochemical sensor chip according to the first embodiment of the present invention;

DETAILED DESCRIPTION OF THE INVENTION

An optical waveguide type biochemical sensor chip according to embodiments and a method of manufacturing the sensor chip will be explained with reference to the drawings.

FIRST EMBODIMENT

Figure 1:
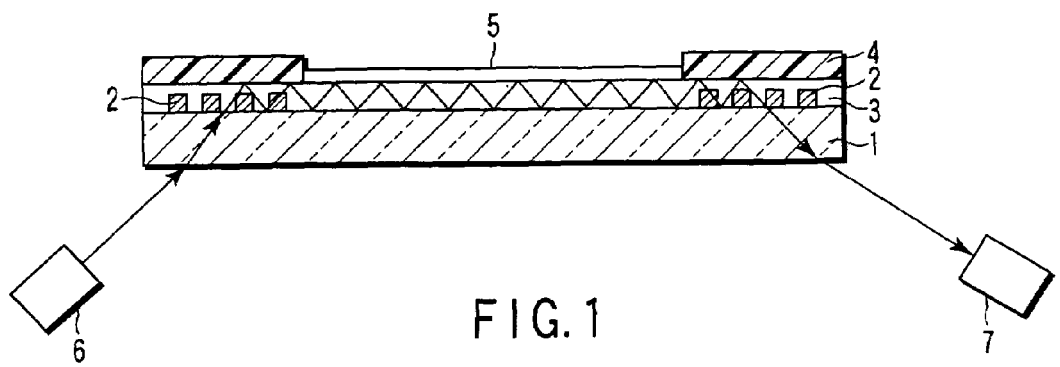
FIG. 1 is a sectional view of an optical waveguide type biochemical sensor chip according to a first embodiment of the present invention.

FIG. 1 is a sectional view of an optical waveguide type biochemical sensor chip according to a first embodiment.

A pair of gratings 2 are formed in each region in the vicinities of both ends of a main surface of a transmittable substrate 1 made of glass (non-alkali glass) or quartz to impinge light beam into the substrate 1 and emit the light beam. These gratings 2 are formed of a material (for example, titanium oxide) having a higher refractive index than the material constituting the substrate 1.

An optical waveguide layer 3 is formed adjacent to the main surface of the substrate 1 on which the above grating 2 is formed, so as to be in close contact with the main surface. This optical waveguide layer 3 is made of a polymer resin having a higher refractive index than the substrate 1 and has a uniform thickness designed to be in the range from 3 to 300 µm.

A protective film 4 is formed adjacent to the surface of the optical waveguide layer 3 so as to cover the region corresponding to each of the above gratings 2 disposed at both ends of the optical waveguide layer 3 corresponding to the region where the grating 2 is formed. This protective film 4 is made of a material (for example, fluororesin) which has a lower refractive index than the material constituting the optical waveguide layer 3 and does not react with any of reagents poured into the sensor chip.

The sensing membrane 5 is positioned in the region sandwiched between the protective films 4 on a line connecting the gratings 2 to each other and formed adjacent to the surface of the optical waveguide layer 3 so as to be in close contact with the surface. This sensing membrane 5 has a biomolecule recognition function and an information transformation function. The sensing membrane 5 is specifically a film creating a reaction product having a specified concentration corresponding to a specimen having a specified concentration and introduced thereon. The reaction product is of such a nature that it acts with light beam propagated in the optical waveguide type biochemical sensor chip or with an evanescent wave emitted from this light beam to consume energy, absorbs the light beam or emits fluorescent light beam.

In the sensing membrane having such a function, the membrane body has a porous structure, and a labeled antibody that is combined with a specimen by an antigen-antibody reaction, a reagent which reacts with the label to generate a reaction product, a catalyst promoting the reaction between the label and the reagent are combined appropriately corresponding to the type of chemical and stored separately in pores formed in the porous structure. A solvent of a specimen solution breaks the structure of the film to release these sensing membranes constituting materials such that these materials freely move, thereby promoting the reaction with the specimen.

When the above sensing membrane 5 is, for example, a glucose sensing membrane, it includes a color-producing reagent, an enzyme for oxidizing or reducing glucose, a reagent which generates a substance for coloring the color-producing reagent by reacting with a product of the enzyme, a membrane forming polymer resin and, as required, a water permeable promoter such as polyethylene glycol. The oxidizing enzyme, regent and color-producing reagent in the glucose sensing membrane are used in the combinations shown in the following Table 1.

photodiode) 7 are disposed on the left side and right side of the backside of the substrate 1 of the biochemical sensor chip, respectively. When laser light beam is impinged to the backside of the substrate 1 of the biochemical sensor chip from the above laser diode 6, the laser light beam propagates as follows: it is refracted in the interface between the grating 2 and the optical waveguide layer 3 after passing through the substrate 1, and refracted by the interfaces between the optical waveguide layer 3 and the substrate 1 or the sensing membrane 5 plural times. At this time, the evanescent wave of the light beam propagated in the optical waveguide layer 3 is absorbed according to a change (for example, a change in absorbance) based on a biochemical reaction of the biomolecule contained in the specimen in the sensing membrane 5, when it is refracted on the substrate-sensing membrane 5 interface.

The light beam that has been propagated in the optical waveguide layer 3 is emitted from the backside of the substrate 1 through the right-side grating 2 and received in the photodiode 7. The intensity of the received light beam becomes a value lower than the light beam intensity (initial light beam intensity) received when the sensing membrane 5 does not enter into a biochemical reaction with the biomolecule and it is possible to detect the amount of biomolecules from the ratio of a reduction in the value.

As to such an optical waveguide layer 3, its thickness is designed to be in the range from 3 to 300 μm due to the following reason.

In a planar optical waveguide type biochemical sensor chip, along with a decrease in the thickness of the optical

TABLE 1

| | Glucose enzyme | Reagent generating substance allowing color-producing reagent to color | Color-producing reagent |
|---|---|---|---|
| Oxidizing enzyme | Glucose oxidase | Peroxidase | 3,3',5,5'-tetramethylbenzidine<br>N,N'-bis(2-hydroxy-3-sulfopropyl)tolidine<br>3,3'-diaminobenzidine |
| | Hexokinase | Glucose-6-phosphoric acid dehydrogenase | 3-(4,5-dimethyl-2-thiazolyl)-2,5-diphenyl-2H-tetrazolium bromide<br>2-(4-rhodophenyl)-3-(2,4-dinitrophenyl)-5-(2,4-disulfophenyl)-2H-tetrazolium<br>3-3'-[3,3'-dimethoxy-(1,1'-biphenyl)-4,4'-diyl]bis(2,5-diphenyl)-2H-tetrazolium choloride |
| Reducing enzyme | Glucose dehydrogenase | Phosphorus molybdate | Aminobenzoic acid |

Examples of the membrane forming polymer resin in the above glucose sensing membrane include cellulose type polymer resins such as carboxymethyl cellulose and hydroxyethyl cellulose.

As the color-producing reagent in the above glucose sensing membrane, 3,3',5,5'-tetramethylbenzidine (TMBZ) that has low solubility in water and is very reduced in harmfulness to organisms is preferably used.

The action of the aforementioned optical waveguide type biochemical sensor chip shown in FIG. 1 will be explained.

A specimen containing a biomolecule is brought into contact with the sensing membrane 5 of the biochemical sensor chip to extract the biomolecule from the specimen to the sensing membrane 5. This biomolecule enters into a biochemical reaction with the sensing membrane 5.

In this situation, a light source (for example, a laser diode) 6 and a light beam receiving element (for example, a waveguide layer, the number of reflections on the surface and interface in the optical waveguide layer is increased, which allows the light beam intensity to attenuate largely. As a result, though measuring sensitivity is improved, a high power light source is required on the contrary to obtain a practical emitting light beam intensity, and it is therefore difficult to realize a small-sized measuring system.

When the reflecting angle at the interface of the substrate and the optical waveguide layer and at the surface of the waveguide layer is θ, the length of the optical waveguide layer (distance between the gratings) is L, and the thickness of the optical waveguide layer is t, the number of reflections n is given by: $n=L/(t \times \tan\theta)$. When the average attenuation factor due to diffusion on the interface and on the surface in the situation where no specimen is allowed to act is α (0), the intensity of incident light beam is I, an attenuation factor caused by the diffraction efficiency at the gratings and diffusion in places except for the inside of the optical waveguide layer is c, and an offset component due to extraneous light beam which does not pass through the optical waveguide is β, the intensity I (0) of emitting light beam in the state where no specimen is allowed to act on the sensing membrane is given by the following equation (1).

$$I(0)=cI(1-\alpha(0))^n+\beta \quad (1)$$

Figure 2:
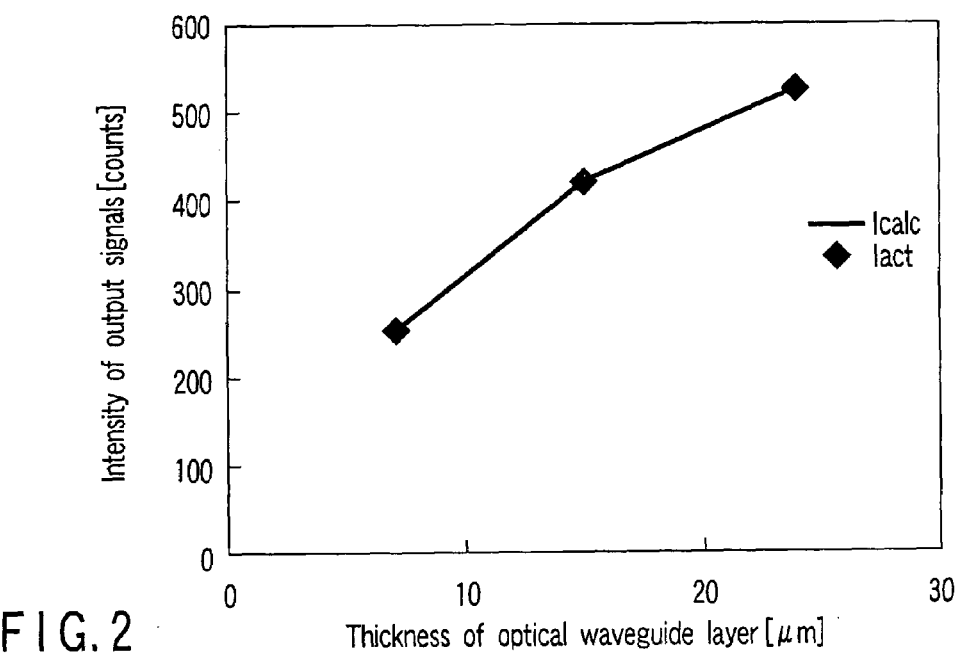
FIG. 2 is a graph showing the dependency of output intensity on the film thickness of an optical waveguide layer in the optical waveguide type biochemical sensor chip according to the first embodiment of the present invention.

FIG. 2 is a graph showing the dependency of the intensity I of output signals on the thickness of the optical waveguide layer in the first embodiment. In FIG. 2, Iact and Icalc represent the actual value and calculated value of the intensity of output signals, respectively. As can be clearly seen from FIG. 2, the intensity of emitted light beam is lowered as the thickness of the optical waveguide layer is decreased.

In the first embodiment, the ratio (R) of reduction in output signals for 180 seconds since the specimen is made to act is used as one of the indexes corresponding to concentration of the specimen to be measured. When the average attenuation factor at the interface and surface of the optical waveguide layer 180 seconds after the specimen is allowed to act is α (180), R is given by the following equation (2).

$$R=\{cI(1-\alpha(0))^n-cI(1-\alpha(180))^n\}/\{cI(1-\alpha(0))^n+\beta\} \quad (2)$$

Figure 3:
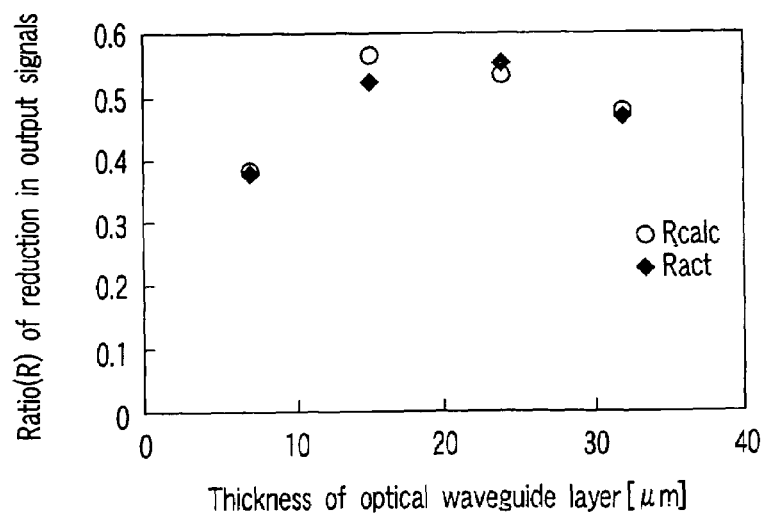
FIG. 3 is a graph showing the dependency of the ratio of a reduction in output signals on the film thickness of an optical waveguide layer in the optical waveguide type biochemical sensor chip according to the first embodiment of the present invention.

FIG. 3 is a graph showing the dependency of the ratio R of reduction in output signals on the thickness of the optical waveguide layer in this embodiment. In FIG. 3, Ract and Rcalc represent the actual value and calculated value of the ratio R of reduction in output signals, respectively. It is found that the ratio of reduction in output signals is not increased as the thickness of the optical waveguide layer is decreased, namely, as the number of reflections in the optical waveguide layer is increased, but takes a maximum value for the thickness of the optical waveguide layer by a reduction in the intensity (I (0)) of initial signals and by the presence of offset components.

In the first embodiment, I (0) and the dependency of the ratio R of reduction in output signals on the thickness of the optical waveguide layer in the case of a specimen having a glucose concentration of 1.0 mg/dL were examined when L=7 mm and θ=78.8°, and the above equations (1) and (2) were applied to these obtained data, respectively. As a result, it was estimated that cI=645, β=155, α (0)=0.0095 and α (180)=about 0.033.

In FIGS. 2 and 3, Icalc and Rcalc are those described as the calculated values of the intensity of output signals and the ratio of reduction in output signals, respectively. The calculated values agreed well with the actual values.

FIG. 4 is a graph obtained by finding α (180) at each glucose concentration of 0.02, 0.1, 0.2, 0.5 and 5 mg/dl and using these constants to plot R as a factor of the thickness of the optical waveguide layer. It is understood from the graph of FIG. 4 that the maximum value of the ratio R of reduction in output signals is shifted to the thicker side with an increase in the concentration of glucose. A calibration curve obtained by plotting the ratio R of reduction in output signals with respect to the concentration of glucose has high linearity on only the low concentration side when the thickness of the optical waveguide layer is about 10 μm or less, and it can be estimated that R at a lower glucose concentration becomes smaller (more reduced sensitivity) as the optical waveguide layer will become thicker and linearity up to a higher concentration will be improved.

The following Table 2 shows the value of the ratio R of reduction in output signals at each glucose concentration and $r^2$ indicating the linearity of the calibration curve in each concentration range as a factor of the thickness of the optical waveguide layer.

TABLE 2

| Optical waveguide layer [μm] | Ratio of reduction in output signals (R) | | | | | | $r^2$ | | |
| --- | --- | --- | --- | --- | --- | --- | --- | --- | --- |
| | 0.02 mg/dl | 0.1 mg/dl | 0.2 mg/dl | 0.5 mg/dl | 1 mg/dl | 5 mg/dl | 0–5 mg/dl | 0–1 mg/dl | 0–0.2 mg/dl |
| 1 | 0.0000 | 0.0000 | 0.0000 | 0.0000 | 0.0000 | 0.0000 | 0.124 | 0.323 | 0.737 |
| 2 | 0.0016 | 0.0045 | 0.0053 | 0.0055 | 0.0055 | 0.0055 | 0.173 | 0.438 | 0.878 |
| 3 | 0.0095 | 0.0321 | 0.0428 | 0.0480 | 0.0481 | 0.0481 | 0.219 | 0.537 | 0.934 |
| 4 | 0.0200 | 0.0742 | 0.1068 | 0.1301 | 0.1322 | 0.1322 | 0.259 | 0.619 | 0.960 |
| 5 | 0.0281 | 0.1099 | 0.1669 | 0.2196 | 0.2276 | 0.2279 | 0.295 | 0.684 | 0.973 |
| 6 | 0.0327 | 0.1328 | 0.2097 | 0.2945 | 0.3133 | 0.3145 | 0.327 | 0.736 | 0.981 |
| 7 | 0.0346 | 0.1448 | 0.2355 | 0.3497 | 0.3827 | 0.3860 | 0.356 | 0.777 | 0.986 |
| 8 | 0.0350 | 0.1495 | 0.2488 | 0.3872 | 0.4363 | 0.4433 | 0.383 | 0.811 | 0.989 |
| 9 | 0.0345 | 0.1498 | 0.2539 | 0.4111 | 0.4768 | 0.4890 | 0.409 | 0.839 | 0.991 |
| 10 | 0.0335 | 0.1475 | 0.2538 | 0.4251 | 0.5068 | 0.5257 | 0.433 | 0.861 | 0.993 |
| 11 | 0.0322 | 0.1437 | 0.2504 | 0.4320 | 0.5286 | 0.5555 | 0.457 | 0.880 | 0.994 |
| 12 | 0.0309 | 0.1392 | 0.2452 | 0.4339 | 0.5439 | 0.5801 | 0.479 | 0.895 | 0.995 |
| 13 | 0.0296 | 0.1344 | 0.2389 | 0.4324 | 0.5542 | 0.6006 | 0.501 | 0.908 | 0.996 |
| 14 | 0.0284 | 0.1295 | 0.2321 | 0.4283 | 0.5606 | 0.6179 | 0.522 | 0.919 | 0.996 |
| 15 | 0.0271 | 0.1247 | 0.2250 | 0.4227 | 0.5639 | 0.6327 | 0.543 | 0.928 | 0.997 |
| 16 | 0.0260 | 0.1200 | 0.2180 | 0.4159 | 0.5648 | 0.6454 | 0.563 | 0.935 | 0.997 |
| 17 | 0.0249 | 0.1156 | 0.2110 | 0.4083 | 0.5638 | 0.6564 | 0.582 | 0.942 | 0.998 |
| 18 | 0.0239 | 0.1113 | 0.2043 | 0.4004 | 0.5613 | 0.6661 | 0.600 | 0.948 | 0.998 |
| 19 | 0.0230 | 0.1073 | 0.1978 | 0.3922 | 0.5576 | 0.6746 | 0.618 | 0.953 | 0.998 |
| 20 | 0.0221 | 0.1036 | 0.1916 | 0.3839 | 0.5531 | 0.6822 | 0.635 | 0.957 | 0.998 |
| 30 | 0.0158 | 0.0757 | 0.1436 | 0.3086 | 0.4880 | 0.7259 | 0.770 | 0.980 | 0.999 |
| 40 | 0.0122 | 0.0592 | 0.1139 | 0.2538 | 0.4232 | 0.7399 | 0.852 | 0.989 | 1.000 |
| 50 | 0.0100 | 0.0485 | 0.0941 | 0.2145 | 0.3701 | 0.7386 | 0.902 | 0.993 | 1.000 |
| 60 | 0.0084 | 0.0411 | 0.0801 | 0.1854 | 0.3276 | 0.7278 | 0.932 | 0.995 | 1.000 |
| 70 | 0.0072 | 0.0356 | 0.0697 | 0.1631 | 0.2932 | 0.7114 | 0.951 | 0.996 | 1.000 |
| 80 | 0.0064 | 0.0314 | 0.0616 | 0.1455 | 0.2651 | 0.6917 | 0.963 | 0.997 | 1.000 |
| 90 | 0.0057 | 0.0281 | 0.0553 | 0.1313 | 0.2418 | 0.6704 | 0.972 | 0.998 | 1.000 |

TABLE 2-continued

| Optical waveguide layer [μm] | Ratio of reduction in output signals (R) | | | | | | $r^2$ | | |
|---|---|---|---|---|---|---|---|---|---|
| | 0.02 mg/dl | 0.1 mg/dl | 0.2 mg/dl | 0.5 mg/dl | 1 mg/dl | 5 mg/dl | 0–5 mg/dl | 0–1 mg/dl | 0–0.2 mg/dl |
| 100 | 0.0051 | 0.0254 | 0.0501 | 0.1196 | 0.2221 | 0.6484 | 0.978 | 0.998 | 1.000 |
| 110 | 0.0047 | 0.0232 | 0.0458 | 0.1098 | 0.2054 | 0.6265 | 0.982 | 0.999 | 1.000 |
| 120 | 0.0043 | 0.0213 | 0.0421 | 0.1015 | 0.1910 | 0.6051 | 0.985 | 0.999 | 1.000 |
| 130 | 0.0040 | 0.0198 | 0.0391 | 0.0944 | 0.1784 | 0.5843 | 0.988 | 0.999 | 1.000 |
| 140 | 0.0037 | 0.0184 | 0.0364 | 0.0881 | 0.1674 | 0.5644 | 0.990 | 0.999 | 1.000 |
| 150 | 0.0035 | 0.0172 | 0.0341 | 0.0827 | 0.1576 | 0.5455 | 0.991 | 0.999 | 1.000 |
| 160 | 0.0033 | 0.0162 | 0.0320 | 0.0779 | 0.1489 | 0.5274 | 0.993 | 0.999 | 1.000 |
| 170 | 0.0031 | 0.0152 | 0.0302 | 0.0736 | 0.1411 | 0.5103 | 0.994 | 0.999 | 1.000 |
| 180 | 0.0029 | 0.0144 | 0.0286 | 0.0698 | 0.1341 | 0.4940 | 0.994 | 1.000 | 1.000 |
| 190 | 0.0027 | 0.0137 | 0.0271 | 0.0663 | 0.1278 | 0.4786 | 0.995 | 1.000 | 1.000 |
| 200 | 0.0026 | 0.0130 | 0.0258 | 0.0632 | 0.1220 | 0.4640 | 0.996 | 1.000 | 1.000 |
| 210 | 0.0025 | 0.0124 | 0.0246 | 0.0603 | 0.1167 | 0.4502 | 0.996 | 1.000 | 1.000 |
| 220 | 0.0024 | 0.0118 | 0.0235 | 0.0577 | 0.1118 | 0.4371 | 0.997 | 1.000 | 1.000 |
| 230 | 0.0023 | 0.0113 | 0.0225 | 0.0553 | 0.1074 | 0.4247 | 0.997 | 1.000 | 1.000 |
| 240 | 0.0022 | 0.0109 | 0.0216 | 0.0531 | 0.1033 | 0.4129 | 0.997 | 1.000 | 1.000 |
| 250 | 0.0021 | 0.0104 | 0.0208 | 0.0511 | 0.0994 | 0.4017 | 0.998 | 1.000 | 1.000 |
| 260 | 0.0020 | 0.0100 | 0.0200 | 0.0492 | 0.0959 | 0.3910 | 0.998 | 1.000 | 1.000 |
| 270 | 0.0019 | 0.0097 | 0.0193 | 0.0474 | 0.0926 | 0.3809 | 0.998 | 1.000 | 1.000 |
| 280 | 0.0019 | 0.0093 | 0.0186 | 0.0458 | 0.0895 | 0.3712 | 0.998 | 1.000 | 1.000 |
| 290 | 0.0018 | 0.0090 | 0.0180 | 0.0443 | 0.0866 | 0.3620 | 0.998 | 1.000 | 1.000 |
| 300 | 0.0018 | 0.0087 | 0.0174 | 0.0429 | 0.0839 | 0.3533 | 0.998 | 1.000 | 1.000 |
| 310 | 0.0017 | 0.0084 | 0.0168 | 0.0415 | 0.0814 | 0.3449 | 0.999 | 1.000 | 1.000 |
| 320 | 0.0016 | 0.0082 | 0.0163 | 0.0403 | 0.0790 | 0.3369 | 0.999 | 1.000 | 1.000 |
| 330 | 0.0016 | 0.0079 | 0.0158 | 0.0391 | 0.0767 | 0.3292 | 0.999 | 1.000 | 1.000 |
| 340 | 0.0015 | 0.0077 | 0.0154 | 0.0380 | 0.0746 | 0.3219 | 0.999 | 1.000 | 1.000 |
| 350 | 0.0015 | 0.0075 | 0.0149 | 0.0369 | 0.0726 | 0.3149 | 0.999 | 1.000 | 1.000 |

Generally, noise components (background amplitude of output signals) in an optical measuring system using laser light beam is a minimum of about 0.3% and a signal variation two to three times the magnitude of the noise components is considered to be necessary to satisfy the lower limit of detection. Therefore, R must be about 0.009 or more. The linearity of the calibration curve is generally regarded as preferable when $r^2 >$ about 0.9.

From the above Table 2, first, the thickness of the optical waveguide layer is fixed to 3 μm to 50 μm from the condition satisfying the following requirements: in a glucose concentration range from 0 to 0.2 mg/dL, R>0.09 and $r^2 >0.9$ when the concentration of glucose is 0.02 mg/dL.

Also, it was determined that an optical waveguide layer having a thickness up to about 300 μm was used based on the condition that high linearity is shown in a glucose concentration range from 0 to 5 mg/dL when the thickness of the optical waveguide layer is 50 μm or more, and the requirement R>0.09 is satisfied when the concentration of glucose is 0.1 mg/dL.

As mentioned above, a restriction on the attenuation of light beam intensity and an improvement in the sensitivity of detection which are antinomic requirements caused by the thickness of the optical waveguide layer can be accomplished by setting the thickness of the optical waveguide layer to 3 to 300 μm.

Such a relatively thick optical waveguide layer can be attained by technologies used to apply a polymer resin solution to a substrate. The thickness of the optical waveguide layer is more preferably 15 to 50 μm from the viewpoint of fulfilling the high linearity at a glucose concentration of 0 to 1 mg/dL and high detection ability indicated by R>0.009 at a glucose concentration of 0.02 mg/dL.

The provision of the optical waveguide layer having the above thickness makes it possible to attain an optical waveguide type biochemical sensor enabling the quantitative detection of glucose having a concentration as extremely low as 0.1 mg/dL or less under the high linearity of the calibration curve.

In the case of using a grating with irregularities having a rectangular sectional shape in the first embodiment, the condition under which the highest coupling efficiency is obtained is given by the following equation (3), when the wavelength of the light beam to be used is λ, the refractive indexes of the concave portion and convex portion of the grating are n11 and n12, respectively, and the height of the grating is d.

$$\lambda/2 = |n11 - n12| \cdot d \quad (3)$$

Also, in the first embodiment, the grating formed on the surface of the substrate is covered with the optical waveguide layer and a protective layer made of a resin having a lower refractive index than that of the optical waveguide layer is formed on the upper surface of the optical waveguide layer. Such a structure can prevent the attenuation caused by the diffusion of light beam associated with damage and contamination to the grating.

The grating having a submicron size structure can be formed with high accuracy by, for example, a combination of lithographic techniques and dry etching techniques. At this time, the rate of etching glass or metal oxide is by no means high and it may take several minutes to etch to a depth of 100 nm. There is therefore a fear that etching to a depth of, for example, 1 μm results in high process cost.

In the first embodiment, a polymer resin having a refractive index n1 of 1.57 is used as the optical waveguide layer to allow light beam having a wavelength of 650 nm to propagate. It is therefore practical to form the grating by allowing d (height of the grating) in the above formula (3) to satisfy d<1 μm and by forming a lattice-like pattern on a film having a refractive index n2 meeting the relationship given by the following equation (4).

$$|n1 - n2| > 0.3275 \quad (4)$$

In the above optical waveguide layer, the length L of the optical waveguide layer (distance between the gratings) is preferably made to be shorter to reduce the attenuation factor. Since the spot diameter of laser light beam is about 0.5 to 1.0 mm, the length of the optical waveguide layer is preferably designed to be 3 mm or more and more preferably 5 to 20 mm in consideration of case of handling and alignment margin.

Generally, a V-parameter is known as the parameter showing propagation characteristics in a three-layer planar optical waveguide and the system is in a single mode when $V<\pi/2$. The V-parameter is given by the following equation (5) when the thickness of the optical waveguide layer is $m\lambda$ (m: integer and $\lambda$: wavelength of propagated light beam).

$$V = m \cdot \pi \cdot (n1^2 - n2^2)^{1/2} \quad (5)$$

Where n1: refractive index of the core layer and n2: refractive index of the clad layer.

When the aforementioned values, $\lambda=655$ nm, n1=1.57 and n2=1.52 are used to calculate the above equation (5), it comes that V=1.2 m, showing that the number of modes allowable in an optical waveguide layer having a thickness four times or less the wavelength of the light beam to be used is 2 or less. Accordingly, the intensity of the light beam to be emitted is largely changed in correspondence to a slight beam change in incident angle. It is therefore necessary to adjust the optical axis strictly to carry out stable measurement.

In the first embodiment, the thickness of the optical waveguide layer is designed to be five times or more the wavelength of the light beam to be used. As a result, it is possible to propagate light beam in a multi mode. Further, as a result of the use of diffused light beam or converged light beam as the light source, it is possible to suppress a variation in the intensity of light beam to be emitted in correspondence to a slight beam change in incident angle.

The aforementioned optical waveguide layer preferably has a hydrophilic functional group such as a hydroxy group, aldehyde group and carboxy group in the surface thereof. The foregoing sensing membrane is satisfactorily stuck to the surface of the optical waveguide layer having such a hydrophilic functional group.

Next, a method of manufacturing the optical waveguide biochemical sensor chip according to the first embodiment will be explained with reference to FIGS. 5A to 5D.

First, a film of a material (for example, a titanium oxide film) having a higher refractive index than that of a substrate 11 which is a transmittable plane spread like a wafer and made of non-alkali glass or quartz is formed on a main surface of the substrate 11 by sputtering. In succession, the titanium oxide film formed in the above step is partially removed by lithography and dry etching so as to form a lattice pattern at a predetermined pitch, thereby forming plural gratings 12 as shown in FIG. 5A. At this time, all the gratings 12 are respectively formed such that they are of the same length at the same pitch. These gratings 12 allow extraneous light beam to be impinged to the inside of the optical waveguide layer and allow the light beam to emit externally (to the substrate side) when the light beam propagated in the optical waveguide layer reaches the gratings 12.

Next, as shown in FIG. 5B, a polymer resin material that has a higher reflectance than that of the material constituting the transmittable substrate 11 and is likewise transmittable is applied to the entire surface of the principal plane of the transmittable substrate 11 on which the gratings 12 are formed in a uniform film thickness by a spin coater and dried, to thereby form an optical waveguide layer film 13 made of polymer resin material and having a thickness of 3 to 300 µm.

Figure 5C:
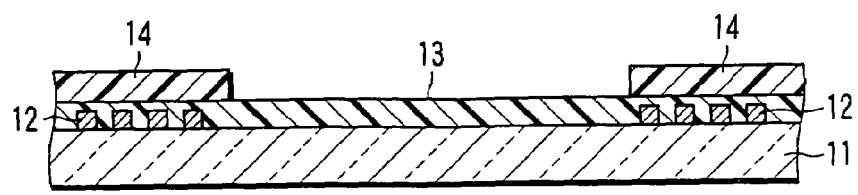

Next, as shown in FIG. 5C, a material, for example, a fluororesin material, that has a lower refractive index than that of the material constituting the optical waveguide layer and does not react with a reagent is formed on the surface part of the optical waveguide layer 13 which corresponds to the region in which the grating 12 is formed by screen printing and dried to form a protective film 14. At this time, the operations are carried out such that the protective film is not formed on the region where the sensing membrane is to be formed. This ensures that the protective film 14 is a film having a frame structure enclosing the region where the sensing membrane is to be formed.

Figure 5D:
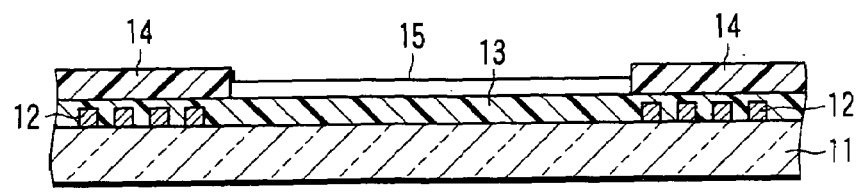

Then, the optical waveguide layer 13 and the protective film 14 are washed. Specifically, the surfaces of the optical waveguide layer 13 and protective film 14 are irradiated with excimer ultraviolet light beam (for example, a wavelength of 172 nm), then dipped in an alkaline solution and washed with pure water. Since impurities such as a fluororesin exist on the surface of the region unprotected with the protective film, they are removed. Then, the substrate 11 is cut up into pieces to form chips by dicing. At this time, the region where the sensing membrane is to be formed and the pair of gratings 12 disposed to sandwich this region are combined as a unit and the substrate 11 is cut up into pieces such that this unit of the structural elements remains in each piece. In succession, the membrane-forming coating solution described in the aforementioned Table 1 is dripped on the region (region where the sensing membrane is to be formed) where the protective film 14 is not formed. The coating solution is dried to form a sensing membrane 15 in the region which is positioned between the gratings 12 and in which the protective film 14 is not formed as shown in FIG. 5D.

By the above process, the optical waveguide type biochemical sensor chip is completed.

According to the first embodiment explained above, a planar optical waveguide type biochemical sensor chip can be obtained in which the measuring system can be small-sized and which makes it simple to carry out an operation of measuring a specimen. Specifically, a restriction on the attenuation of light beam intensity and an improvement in the sensitivity of detection which are antinomic requirements can be accomplished by setting the thickness of the optical waveguide layer to 3 to 300 µm The optical waveguide layer having such a thickness can secure sufficient transmittance. Also, the formation of the grating using a material having a refractive index higher by 0.3 or more than that of the optical waveguide layer has succeeded in obtaining high diffraction efficiency even when it has a height as low as 1 µm or less. These characteristics make it possible to use a small-sized and inexpensive laser diode having a relatively low power as a light source.

Moreover, the grating is formed on the surface of the substrate and covered with the optical waveguide layer, and the part of the surface of the optical waveguide layer which is positioned above the grating is coated with a material having a refractive index lower than that of the optical waveguide layer, which ensures that damages and contaminations to the coupling function elements can be suppressed.

Also, the thickness of the optical waveguide layer is designed to be five times or more the wavelength of the light source to be used, which has brought about the situation where waveguide light beam is propagated in a multi-mode in the optical waveguide layer. In addition, the use of diffused light beam or converged light beam as the light source has brought about the situation where it is possible to suppress a variation in the intensity of light beam to be emitted in correspondence to a slight beam change in incident angle.

SECOND EMBODIMENT

Figure 6:
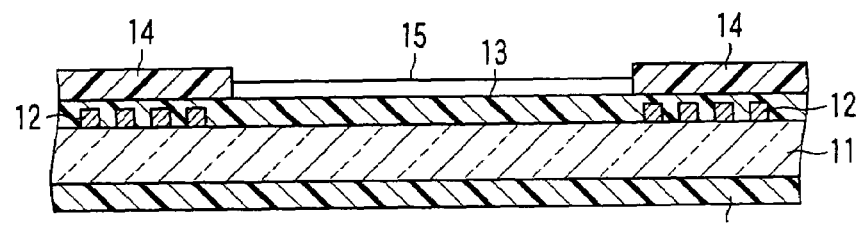
FIG. 6 is a sectional view of an optical waveguide type biochemical sensor chip according to a second embodiment of the present invention.

FIG. 6 is a sectional view of an optical waveguide type biochemical sensor chip according to a second embodiment.

A pair of gratings 12 are formed in each region in the vicinities of both ends of a main surface of a substrate 11 made of glass (for example, non-alkali glass) or quartz to impinge light beam into the substrate 11 and emit the light beam. These gratings 12 are formed of a material, for example, titanium oxide, having a higher reflectance than that of the substrate 11. An optical waveguide layer 13 which is formed of a polymer resin having a higher refractive index than that of the substrate 11 and has a thickness of 3 to 300 μm is formed on the main surface of the substrate 11 including the above gratings 12. A protective film 14 made of a material (for example, a fluororesin) which has a low refractive index and does not react with a regent is formed in each vicinity of both ends of the optical waveguide layer 13 which corresponds to the grating 12, i.e., positions corresponding to the grating 12.

A sensing membrane 15 having a biomolecule recognition function and an information transformation function is formed on the part positioned between the protective films 14 on the optical waveguide layer 13.

The foregoing structure is the same as that of the first embodiment. In the second embodiment, a polymer resin layer 16 having the same material and the same thickness as the above optical waveguide layer 3 is formed on the entire surface of the backside of the substrate 11, that is, the main surface on the side of the substrate 11 on which the optical waveguide layer 13 is not formed such that it is stuck to and disposed adjacent to the backside surface.

Such an optical waveguide type biochemical sensor chip according to the second embodiment can detect the quantity of biomolecules in a specimen in the same operation as in the case of the sensor chip shown in the first embodiment. Also, the optical waveguide type biochemical sensor can limit the warpage thereof caused by extraneous factors such as a variation in temperature by using a simple structure, enabling the formation of a measuring system structure resistance to disturbances.

The thickness range of the optical waveguide layer is limited to 3 to 300 μm, for the same as reason as that explained in the first embodiment. The thickness of the optical waveguide layer is more preferably 15 to 50 μm.

In the optical waveguide layer 13 having the above thickness, the length (length of the interval between the gratings) of the optical waveguide layer is preferably 3 mm or more and more preferably 5 to 20 mm.

The aforementioned optical waveguide layer preferably has a hydrophilic functional group such as a hydroxy group, aldehyde group and carboxy group in the surface thereof. The foregoing sensing membrane is satisfactorily stuck to the surface of the optical waveguide layer having such a hydrophilic functional group.

When the above sensing membrane is, for example, a glucose sensing membrane, it includes a color-producing reagent, an enzyme for oxidizing or reducing glucose, a reagent which generates a substance for coloring the color-producing reagent by reacting with a product of the enzyme, membrane forming polymer resin (cellulose type polymer resins such as carboxymethyl cellulose and hydroxycellulose) and, as required, a water permeable promoter such as polyethylene glycol. The color-producing reagent, oxidizing enzyme and regent in the glucose sensing membrane are used in the combinations shown in the aforementioned Table 1.

Next, a method of manufacturing the optical waveguide type biochemical sensor chip according to the second embodiment will be explained with reference to FIGS. 7A to 7E.

Figure 7A:
FIGS. 7A, 7B, 7C, 7D and 7E are sectional views showing steps of producing the optical waveguide type biochemical sensor chip according to the second embodiment of the present invention.

First, a film of a material (for example, a titanium oxide film) having a higher refractive index than that of a substrate 11 made of non-alkali glass or quartz is formed on the principal plane of the substrate 11 by sputtering as shown in FIG. 7A.

In succession, the titanium oxide film is selectively removed by lithography and dry etching to form a grating 12.

Figure 7B:
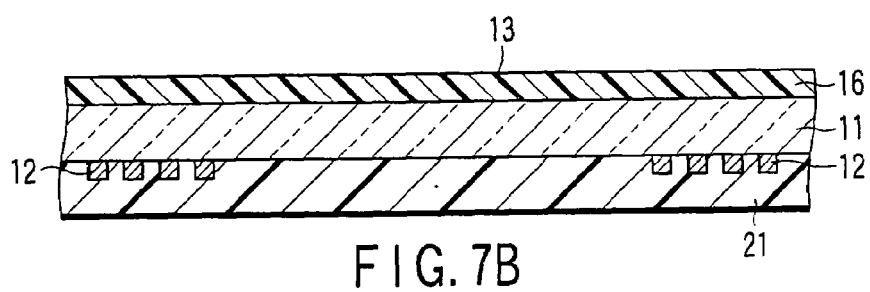

Then, a main surface of the substrate 11 including the grating 12 is coated with a resist film 21 that protects the grating 2. Then, the substrate 11 is turned over and a solution of a polymer resin having a higher refractive index than that of the substrate 11 is applied to the backside of the substrate 11 and dried, thereby forming a polymer resin layer 16 having a thickness of 3 to 300 μm as shown in FIG. 7B.

Figure 7C:
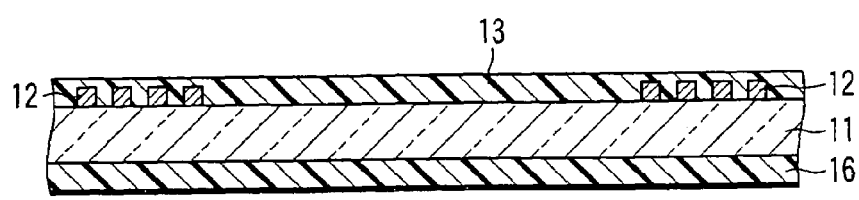

Then, the resist film 21 is peeled and removed and then the substrate 11 is turned over again. A solution of a polymer resin having the same material as the above polymer resin is applied to the entire surface of the substrate 11 including the grating 12 by spin coating or the like and dried, thereby forming an optical waveguide layer 13 having the same thickness as that of the polymer resin layer 16 as shown in FIG. 7C.

Figure 7D:
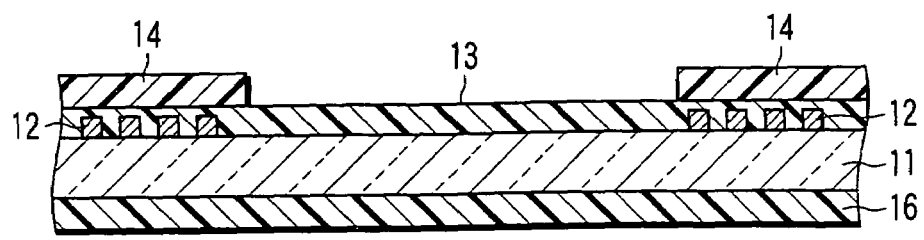

Next, a material, such as a fluororesin material, which has a low refractive index and does not react with a reagent is formed on the surface part of the optical waveguide layer 13 which corresponds to the grating 12 by screen printing and dried, thereby forming a protective film 14 as shown in FIG. 7D.

Next, this substrate 11 is cut into chips by dicing. At this time, impurities such as a fluororesin exist on the surface of the region which is positioned between the protective films and in which the sensing membrane is to be formed, on the optical waveguide layer. Therefore, the substrate 11 is irradiated with excimer ultraviolet light beam having a wavelength of, for example, 172 nm, then dipped in an alkaline solution and washed with pure water.

Figure 7E:
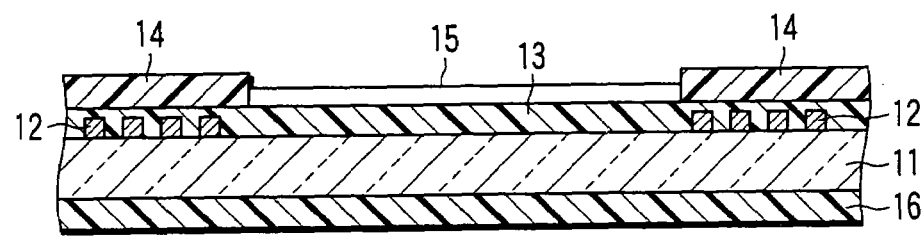

In succession, a membrane-forming coating solution having the components described in the aforementioned Table 1 is dripped on the region which is positioned between the protective films 14 on the surface of the optical waveguide layer 13 and dried, thereby forming a sensing membrane 15 in the region which is positioned between the gratings and in which the protective film is not formed as shown in FIG. 7E.

By the above process, the optical waveguide type biochemical sensor chip according to the second embodiment is completed.

According to the second embodiment explained above, the thickness of the optical waveguide layer is limited to a range from 3 to 300 μm, whereby the incident angle at which light beam can be impinged with the grating for impinging light beam in the first embodiment can be broadened and an optical waveguide type biochemical sensor chip that detects microorganisms by simple operations can be obtained.

In addition, a restriction on the attenuation of light beam intensity and an improvement in the sensitivity of detection which are antinomic requirements can be accomplished by setting the thickness of the optical waveguide layer to 3 to 300 μm. Also, the optical waveguide layer having such a thickness ensures satisfactory transmittance. It is therefore possible to use a small-sized and inexpensive laser diode having a relatively low power as a light source.

Also, the formation of the polymer resin layer 16 having the same material and the same thickness as those of the optical waveguide layer 13 on the backside of the substrate 11 makes the substrate 11 resistant to warpage, thereby allowing light beam to be impinged to the substrate at a regular angle.

Specifically, when the optical waveguide layer 13 made of a polymer resin and having a thickness as relatively high as 3 to 300 μm is formed on a substrate such as glass, there is a fear that, since the coefficient of linear expansion of glass of the substrate 11 is different by one digit from that of the polymer resin of the optical waveguide layer 13, the difference in these coefficients of linear expansion causes warpage of the substrate 1 in the case where the biochemical sensor chip is heated. The occurrence of warpage of the substrate 11 would cause a fluctuation in the incident angle of the substrate 11, with the result that the sensitivity of detection is reduced.

Based on these facts, the polymer resin layer 16 having the same material and the same thickness as those of the optical waveguide layer 13 is formed on the backside of the substrate 11. This enables the prevention of warpage of the substrate 11 because a warpage caused by the difference in the coefficients of linear expansion between the substrate 11 and the optical waveguide layer 13 can be offset by the stress imposed in the opposite direction in the same amount of warpage caused by a difference in the coefficients of linear expansion between the substrate 11 and the polymer resin layer 16 formed on the backside of the substrate 11. As a result, light beam can be impinged to the substrate 11 at a regular angle, and it is therefore possible to maintain a high detection sensitivity.

Moreover, the method according to the second embodiment ensures that the optical waveguide type biochemical sensor chip having the aforementioned excellent characteristics can be manufactured.

Particularly, the polymer resin layer 16 is formed on the backside of the substrate 11 just after the grating 12 is formed, namely, before the optical waveguide layer 13 is formed, whereby damage to the optical waveguide layer 13 can be prevented. In this step, as shown in FIG. 7B, the grating 12 is covered with the easily removable resist film 21. It is therefore possible to protect the grating 12 during spin coating for forming the polymer resin layer 16.

Examples of the present invention will be explained in detail below.

EXAMPLE 1

A titanium oxide film of 50 nm in thickness was formed on a principal plane of a non-alkali glass substrate having a refractive index of 1.52 by sputtering titanium oxide having a refractive index of 2.2 to 2.4. Then, the titanium oxide film was selectively removed by lithography and dry etching (RIE) to form a grating. In succession, a heat-curable resin solution was applied to the principal plane of the glass substrate including the grating by a spin coater and baked to form an optical waveguide layer having a thickness of 25 to 35 μm and a refractive index of 1.57. In succession, a fluororesin was formed on the surface part of the optical waveguide layer which corresponded to the grating by screen printing and dried to form a protective layer.

Then, the substrate was cut into pieces having the dimensions of 17 mm×6.5 mm to make chips. In succession, the region of the optical waveguide layer which was positioned between the protective films was irradiated with excimer ultraviolet light beam having a wavelength of 172 nm, then dipped in an alkaline solution and washed with pure water to provide moderate hydrophilic properties. Then, a glucose sensing membrane-forming coating solution was dripped on the surface of the sensing membrane-forming region positioned between the gratings of the substrate, followed by purging using inert gas and drying under vacuum to form a porous (water permeable) glucose sensing membrane of 0.5 to 1.0 μm in thickness, and the optical waveguide type biochemical glucose sensor shown in FIG. 1 was thus produced. The glucose sensing membrane-forming coating solution had the following composition.

<Composition of Glucose Sensing Membrane-forming Coating Solution>
Phosphoric acid buffer solution: 0.000525 mol/L
Poly(ethylene glycol) (PEG): 0.15 wt %
3,3',5,5'-tetramethylbenzidine (TMBZ): 0.15 mg/dL
Carboxymethyl cellulose (CMC): 0.32 wt %
Peroxidase (POD): 0.0015 mg/dL
Glucose oxidase (GOD): 0.012 mg/dL As shown in FIG. 1, a laser diode 6 and a photodiode 7 were disposed on the left and right sides of the backside of the substrate 1 of the biochemical glucose sensor, respectively. The laser light beam having a wavelength of 655 nm was allowed to be impinged to the left side grating 2 from the laser diode 6, propagated in an optical waveguide layer 3 and emitted from the right side grating 2. A fixed amount of an aqueous glucose solution was dripped on the sensing membrane 5 while measuring the intensity of the light beam by the photodiode 7. The ratio of reduction (sensitivity) in the intensity of laser light beam for a fixed time after the glucose solution was dripped was plotted as a factor of the concentration of glucose. The results are shown in FIG. 8.

Figure 8:
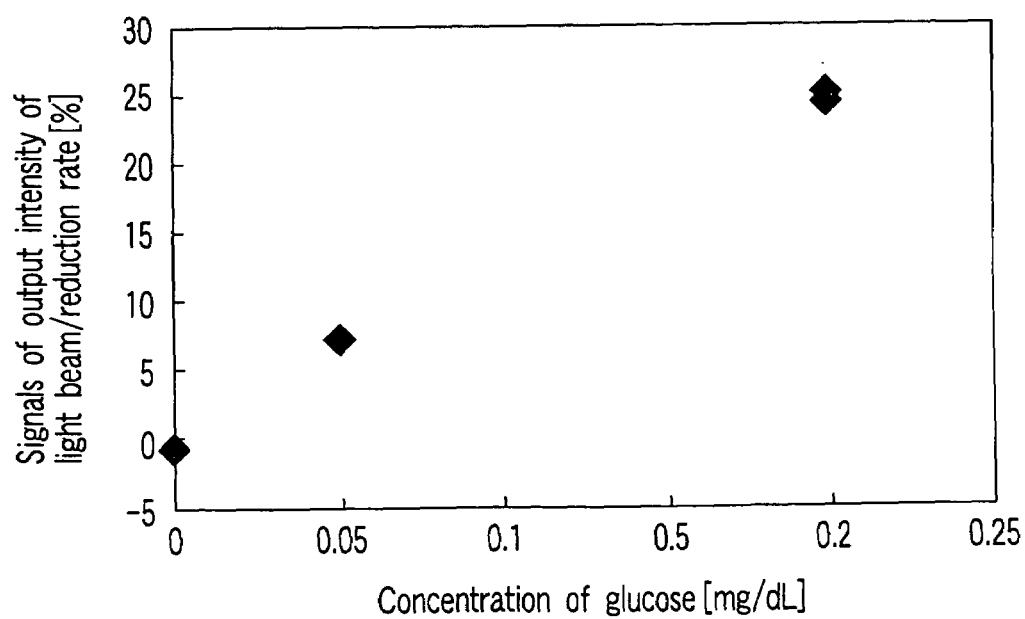
FIG. 8 is a graph showing the relationship between the concentration of glucose and the ratio of a reduction in the intensity of laser light beam (sensitivity).

As is clear from FIG. 8, it is found that the glucose sensor chip of Example 1 can detect glucose having a low concentration with a high sensitivity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical waveguide type biochemical sensor chip comprising:

a light beam transmittable substrate having at least one of a first optical element which allows light beam to be impinged to the inside and a second optical element which emits light beam from the inside;

an optical waveguide layer which is formed on a main surface of the substrate on which at least one of the first and second optical elements is formed, has a thickness of 3 to 300 μm and is made of a polymer resin material having a higher refractive index than that of the substrate material; and a sensing membrane which is formed on the optical waveguide layer and creates a reaction product having the ability of absorbing light beam or an evanescent wave of light beam in response to an introduced specimen.

2. The sensor chip according to claim 1, wherein the first and second optical elements are a grating made of a material having a high refractive index 0.3 or more that of the optical waveguide layer.

3. The sensor chip according to claim 2, wherein the material of the grating includes at least one material selected from the group consisting of titanium oxide, tantalum oxide, indium oxide, tin oxide, zinc oxide, aluminum oxide and silicon nitride.

4. The sensor chip according to claim 1, wherein the length of the optical waveguide layer region where the impinged light beam propagates is 3 mm or more.

5. The sensor chip according to claim 1, wherein the optical waveguide layer has a thickness five times or more the wavelength of the incident light beam and the light beam is propagated in a multi-mode.

6. The sensor chip according to claim 1, wherein a polymer resin layer having the same material and the same thickness as those of the optical waveguide layer is formed also on a surface opposite to the main surface of the substrate.

7. The sensor chip according to claim 1, wherein a protective film made of a material having a lower refractive index than that of the optical waveguide layer is formed also on the surface of the optical waveguide layer.

8. The sensor chip according to claim 1, wherein a frame structure film made of a material having a lower refractive index than that of the optical waveguide layer is formed also on the surface of the optical waveguide layer so as to enclose the sensing membrane.

9. The sensor chip according to claim 1, wherein the sensing membrane contains 3,3',5,5'-tetramethylbenzidine (TMBZ).

10. A method of manufacturing an optical waveguide type biochemical sensor chip, comprising:
    forming at least one of a first optical element which allows light beam to be impinged to the inside and a second optical element which emits light beam from the inside on a light beam transmittable substrate;
    forming an optical waveguide layer of 3 to 300 μm in thickness by applying a polymer resin material having a higher refractive index than that of the substrate on a main surface of the substrate on which at least one of the first and second optical elements is formed, and by drying; and
    forming a sensing membrane which creates a reaction product having the ability of absorbing the light beam or an evanescent wave of the light beam in response to a specimen introduced into the optical waveguide layer.

11. The method according to claim 10, wherein a protective film made of a material having a lower refractive index than that of the optical waveguide is formed also on the surface region of the optical waveguide including at least one of the first and second optical elements.

12. The method according to claim 10, wherein a frame structure film made of a material having a lower refractive index than that of the optical waveguide layer is formed also on the surface of the optical waveguide layer so as to enclose the sensing membrane.

13. The method according to claim 10, wherein at least one of the first and second optical elements is formed in plurality on the main surface of the substrate, the optical waveguide layer is formed and then a cutting operation is carried out.

14. A method of manufacturing an optical waveguide type biochemical sensor chip, comprising:
    forming at least one of a first optical element which allows light beam to be impinged to the inside and a second optical element which emits light beam from the inside on a light beam transmittable substrate;
    forming an optical waveguide layer of 3 to 300 μm in thickness by applying a polymer resin material having a higher refractive index than that of the substrate on a main surface of the substrate on which at least one of the first and second optical elements is formed, and drying;
    forming a polymer resin layer having the same material and the same thickness as those of the optical waveguide layer on a surface opposite to the main surface of the substrate; and
    forming a sensing membrane which creates a reaction product having the ability of absorbing the light beam or an evanescent wave of the light beam in response to a specimen introduced into the optical waveguide layer.

15. The method according to claim 14, wherein a protective film made of a material having a lower refractive index than that of the optical waveguide is formed also on the surface region of the optical waveguide including at least one of the first and second optical elements.

16. The method according to claim 14, wherein a frame structure film made of a material having a lower refractive index than that of the optical waveguide layer is formed also on the surface of the optical waveguide layer so as to enclose the sensing membrane.

17. The method according to claim 14, wherein at least one of the first and second optical elements is formed in plurality on the main surface of the substrate, the optical waveguide layer is formed and then a cutting operation is carried out.

* * * * *